United States Patent
Kawamae et al.

(10) Patent No.: US 12,204,720 B2
(45) Date of Patent: Jan. 21, 2025

(54) FINGER TAPPING MEASUREMENT PROCESSING TERMINAL, SYSTEM, METHOD, AND COMPUTER PROGRAM

(71) Applicant: MAXELL, LTD., Kyoto (JP)

(72) Inventors: Osamu Kawamae, Kyoto (JP); Yoshinori Okada, Kyoto (JP); Tomohiko Mizuguchi, Kyoto (JP)

(73) Assignee: MAXELL, LTD., Kyoto (JP)

( * ) Notice: Subject to any disclaimer, the term of this patent is extended or adjusted under 35 U.S.C. 154(b) by 0 days.

(21) Appl. No.: 18/262,079

(22) PCT Filed: Jan. 13, 2022

(86) PCT No.: PCT/JP2022/000928
§ 371 (c)(1),
(2) Date: Jul. 19, 2023

(87) PCT Pub. No.: WO2022/163364
PCT Pub. Date: Aug. 4, 2022

(65) Prior Publication Data
US 2024/0111380 A1 Apr. 4, 2024

(30) Foreign Application Priority Data
Jan. 26, 2021 (JP) .................................. 2021-010265

(51) Int. Cl.
*G06F 3/041* (2006.01)
*A61B 5/00* (2006.01)
(Continued)

(52) U.S. Cl.
CPC .......... *G06F 3/0418* (2013.01); *A61B 5/0077* (2013.01); *A61B 5/1101* (2013.01);
(Continued)

(58) Field of Classification Search
CPC .... G06F 3/0418; G06F 3/0414; G06F 3/0425; G06F 2203/04104; G06F 2203/04106;
(Continued)

(56) References Cited

U.S. PATENT DOCUMENTS

2010/0106060 A1* 4/2010 Tsuji .................... A61B 5/1101
600/587
2011/0054361 A1* 3/2011 Sakoda ................ A61B 5/4082
600/595
(Continued)

FOREIGN PATENT DOCUMENTS

JP 2010-99263 A 5/2010
JP 2016-049123 A 4/2016
(Continued)

OTHER PUBLICATIONS

International Search Report issued in corresponding International Application No. PCT/JP2022/000928, dated Apr. 5, 2022, w/ English Translation (5 pages).

*Primary Examiner* — Christopher E Leiby
(74) *Attorney, Agent, or Firm* — Rimon P.C.

(57) ABSTRACT

A finger tapping measurement processing terminal that measures a finger tapping motion and processes a measurement result includes: a touch panel that is provided on one surface of a terminal, is capable of displaying information related to the finger tapping motion, and is tapped by one of two fingers of a same hand of a user who holds the terminal; finger detectors that detect a motion of one finger tapping the touch panel; and a processor that performs processing of measuring a two-finger distance during a finger tapping motion between the other of the two fingers holding another surface of the terminal located on an opposite side of the touch panel and the one finger tapping the touch panel based on detection information obtained by the finger detectors.

22 Claims, 12 Drawing Sheets

(51) Int. Cl.
*A61B 5/11* (2006.01)
*G06F 3/042* (2006.01)

(52) U.S. Cl.
CPC .......... *A61B 5/1128* (2013.01); *A61B 5/4064* (2013.01); *A61B 5/4088* (2013.01); *A61B 5/6898* (2013.01); *A61B 5/7278* (2013.01); *A61B 5/743* (2013.01); *A61B 5/7475* (2013.01); *G06F 3/0414* (2013.01); *G06F 3/0425* (2013.01); *A61B 2560/0223* (2013.01); *A61B 2562/0247* (2013.01); *G06F 2203/04104* (2013.01); *G06F 2203/04106* (2013.01)

(58) Field of Classification Search
CPC ... A61B 5/0077; A61B 5/1101; A61B 5/1128; A61B 5/4064; A61B 5/4088; A61B 5/6898; A61B 5/7278; A61B 5/743; A61B 5/7475; A61B 5/11; A61B 2560/0223; A61B 2562/0247; A61B 10/00
See application file for complete search history.

(56) References Cited

U.S. PATENT DOCUMENTS

| | | | |
|---|---|---|---|
| 2011/0267042 A1* | 11/2011 | Sano | A61B 5/1125 324/207.11 |
| 2013/0141373 A1* | 6/2013 | Takuma | G06F 3/04883 345/173 |
| 2014/0320434 A1* | 10/2014 | Pantel | G06F 3/017 345/173 |
| 2015/0351525 A1* | 12/2015 | Sadai | A45F 5/10 294/158 |
| 2016/0073033 A1 | 3/2016 | Ogasawara et al. | |
| 2020/0042323 A1 | 2/2020 | Sano et al. | |
| 2020/0222756 A1 | 7/2020 | Sano et al. | |

FOREIGN PATENT DOCUMENTS

| | | |
|---|---|---|
| JP | 2016-058061 A | 4/2016 |
| JP | 2018-186961 A1 | 11/2018 |
| WO | 2017/212719 A1 | 12/2017 |
| WO | 2018/062173 A1 | 4/2018 |

\* cited by examiner

[Fig. 1]
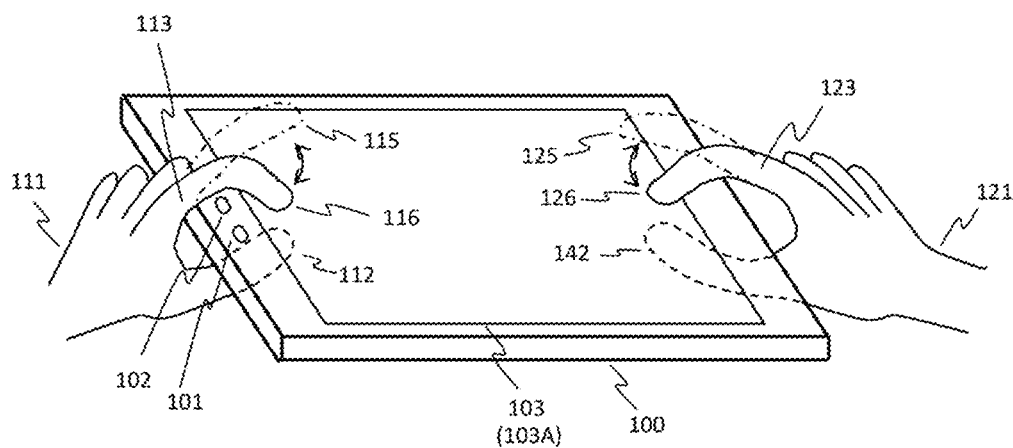
[Fig. 2]
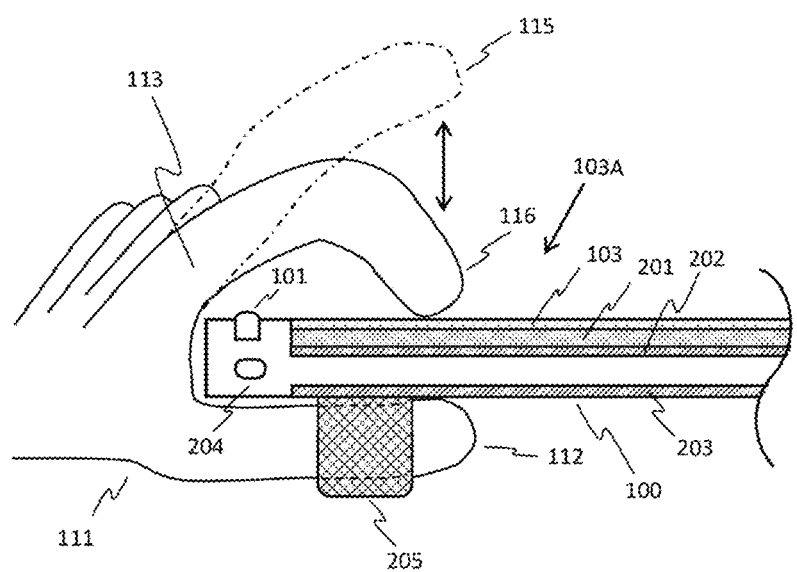

[Fig. 3]
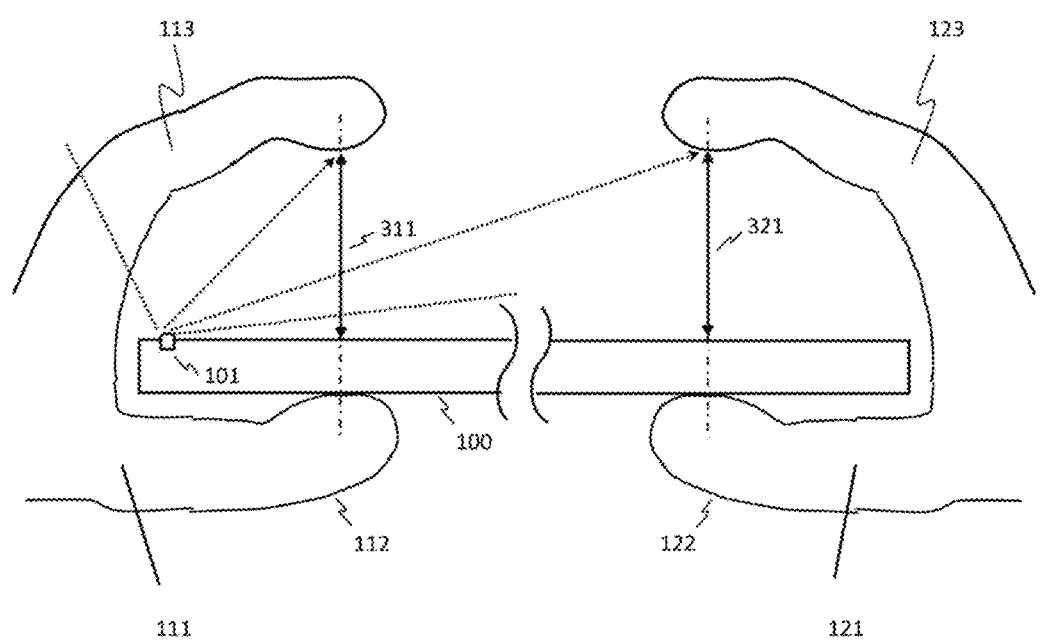

[Fig. 4]
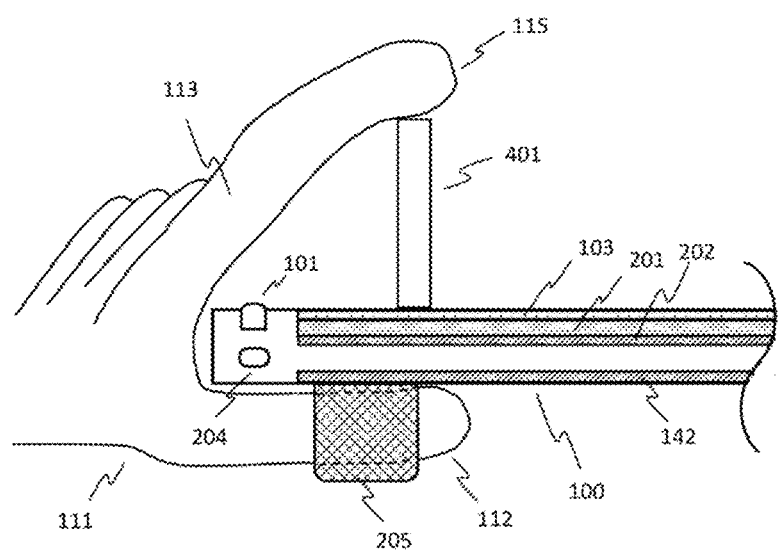

[Fig. 5]
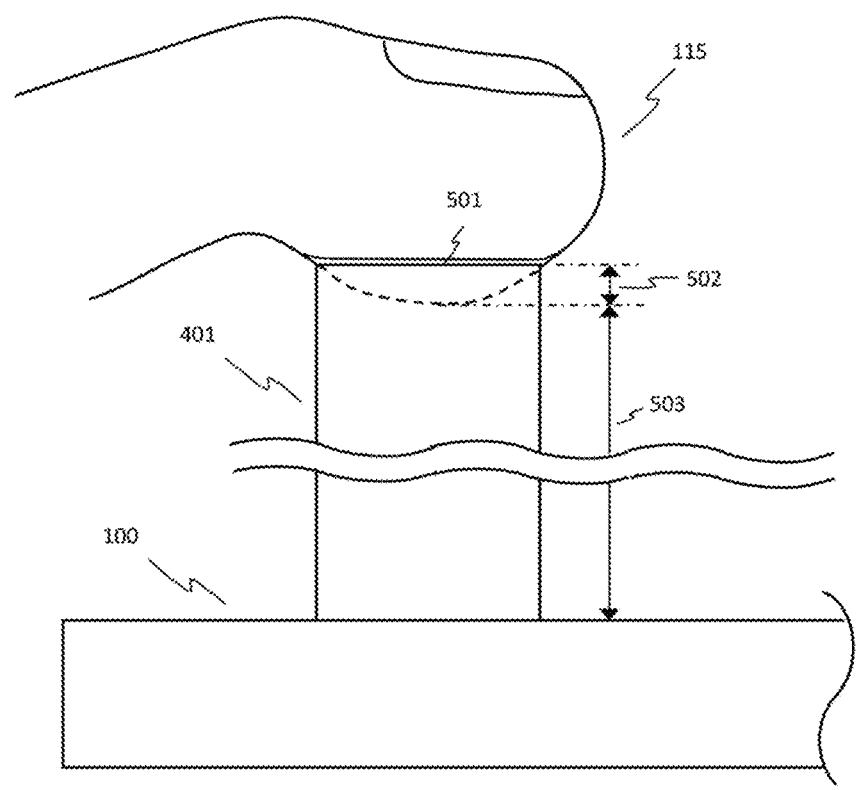

[Fig. 6]
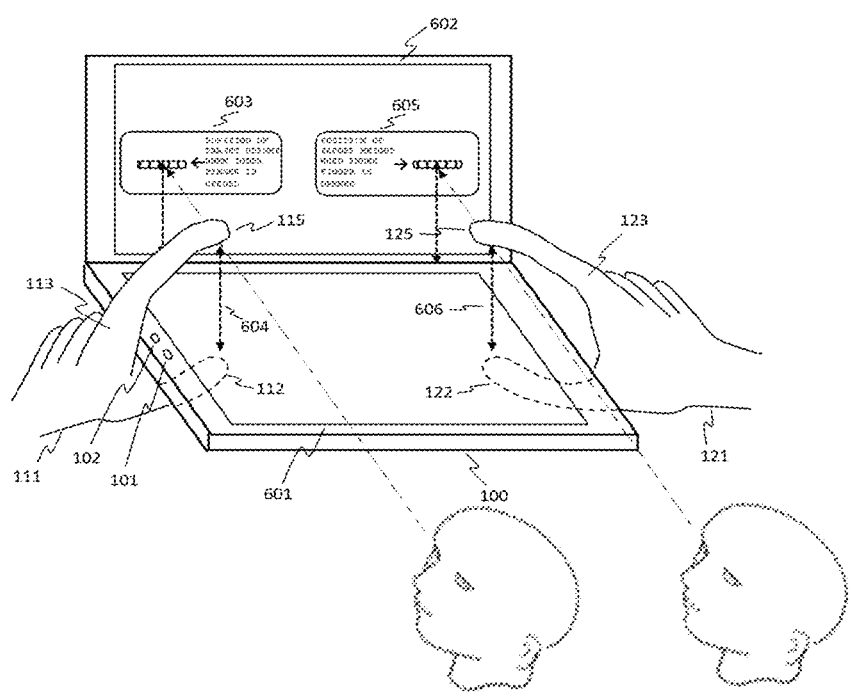

[Fig. 7]
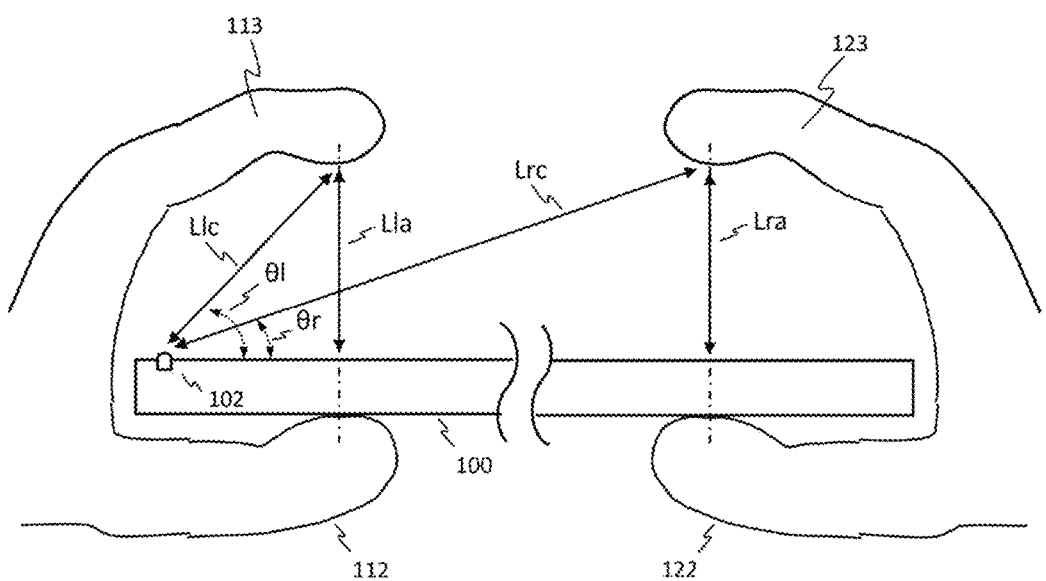

[Fig. 8]
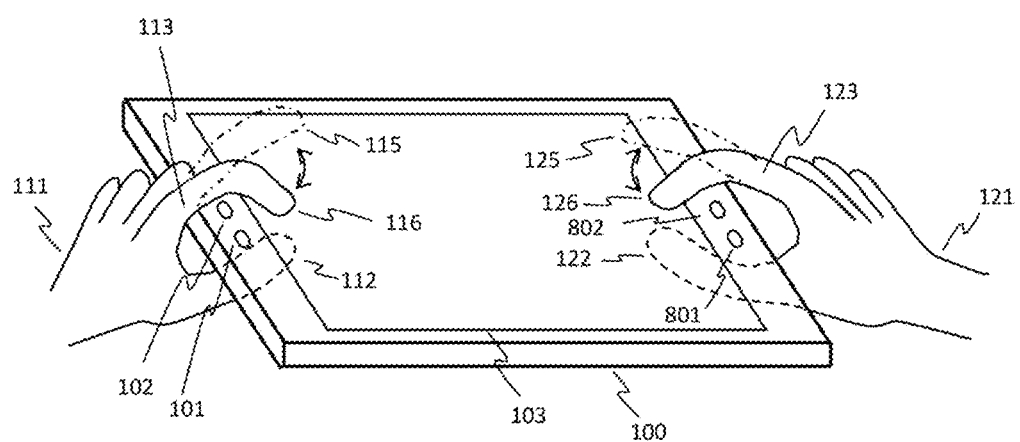

[Fig. 9]
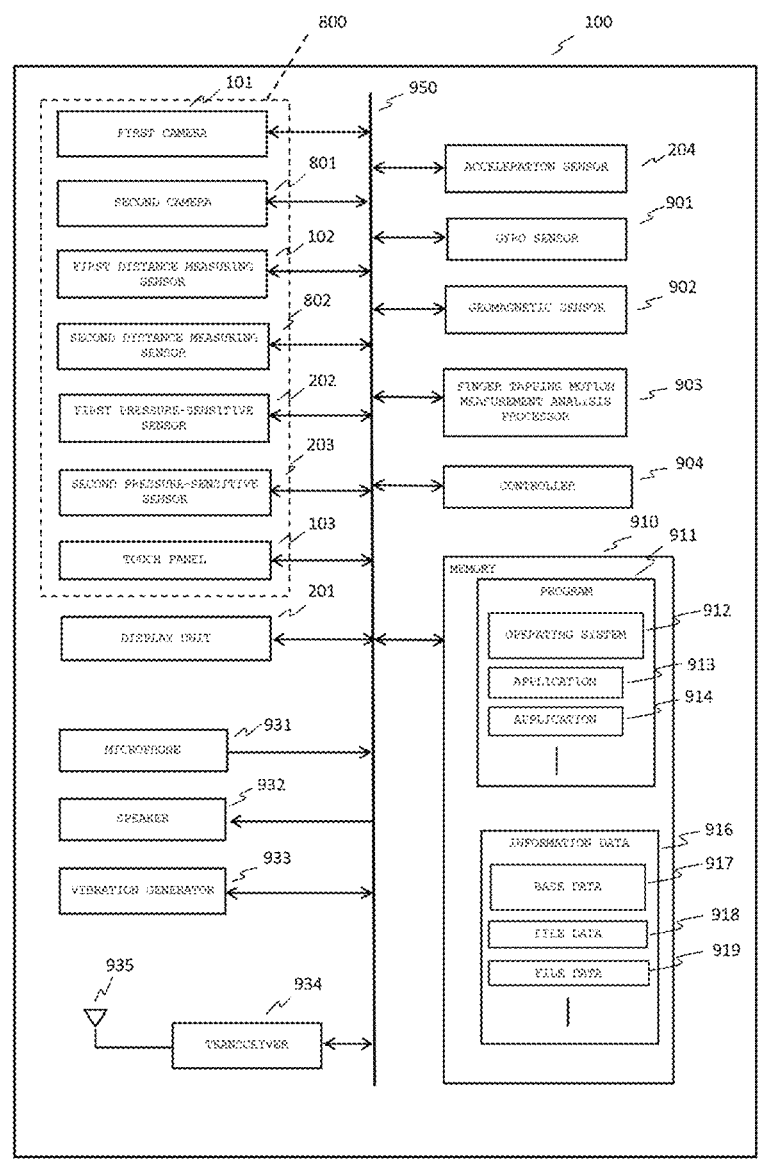

[Fig. 10]
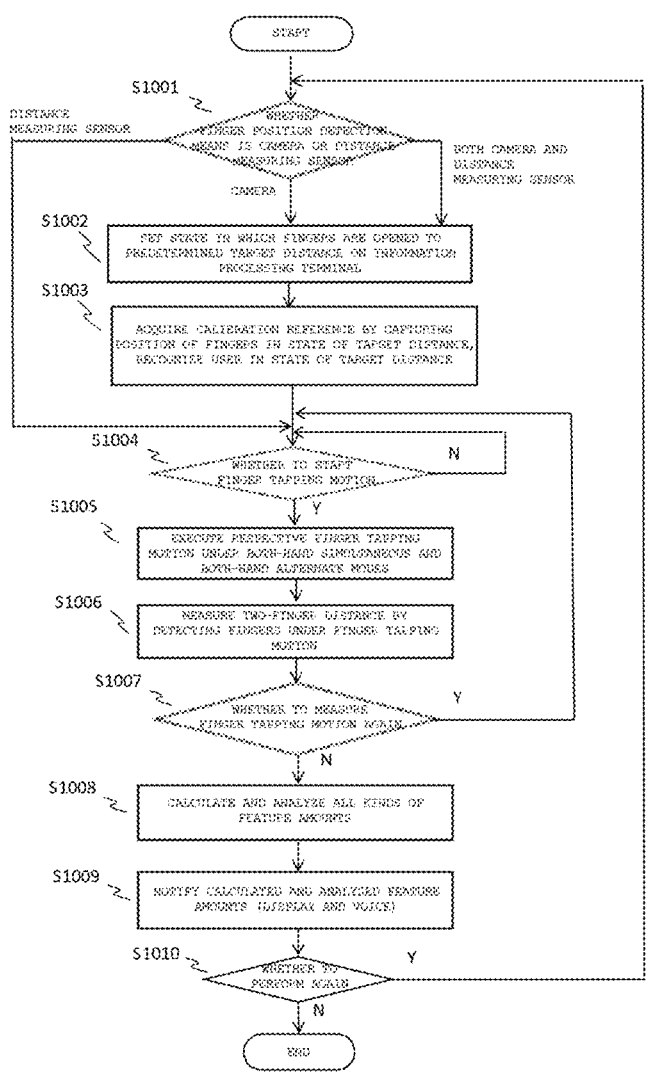

[Fig. 11]
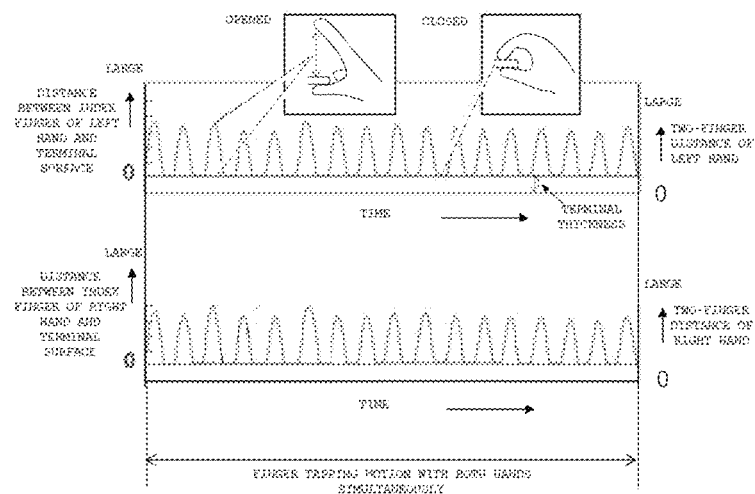
(a)
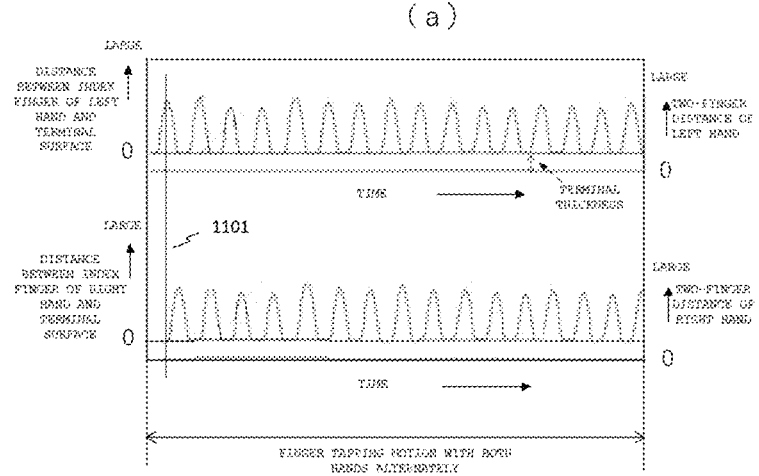
(b)

[Fig. 12]
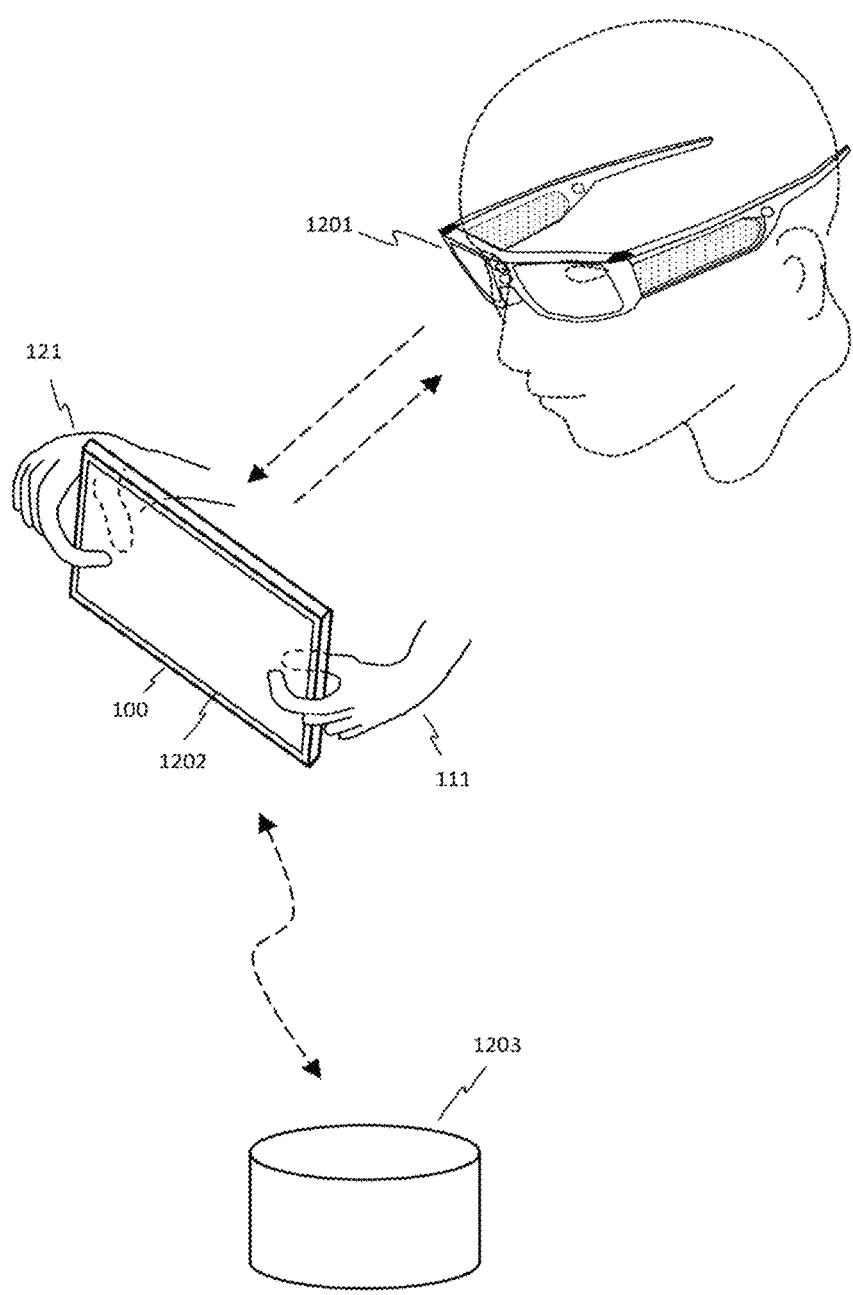

[Fig. 13]
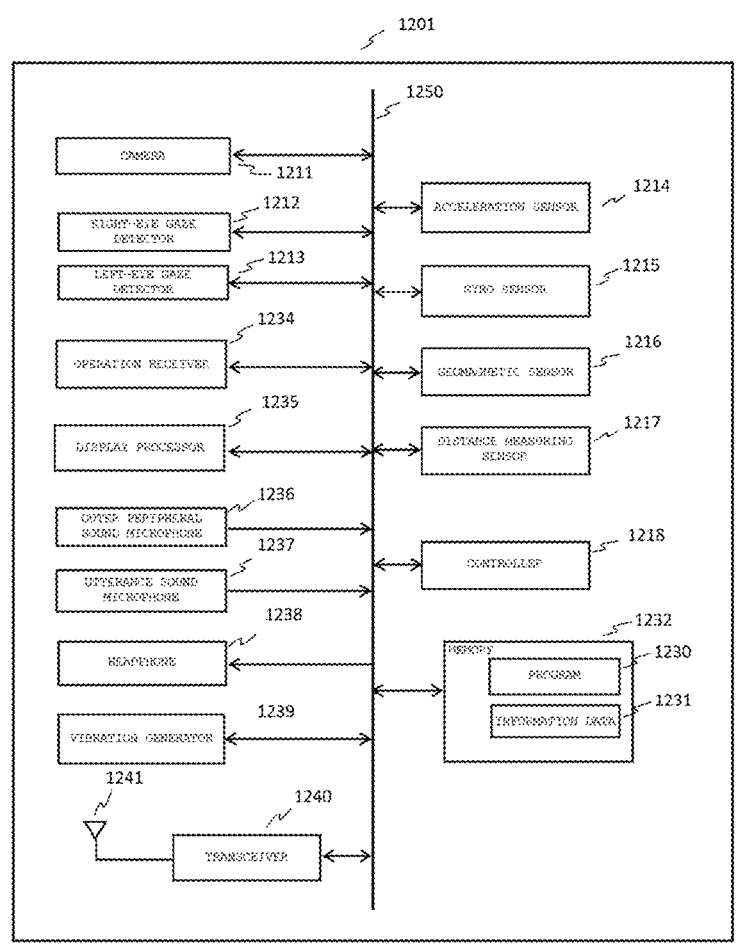

FINGER TAPPING MEASUREMENT PROCESSING TERMINAL, SYSTEM, METHOD, AND COMPUTER PROGRAM

CROSS REFERENCE TO RELATED APPLICATIONS

This application is the U.S. National Phase under 35 U.S.C. § 371 of International Application No. PCT/JP2022/000928, filed on Jan. 13, 2022, which claims the benefit of Japanese Application No. 2021-010265, filed on Jan. 26, 2021, the entire contents of each are hereby incorporated by reference.

TECHNICAL FIELD

The present invention relates to a finger tapping measurement processing terminal, a finger tapping measurement processing system, a method, and a computer program for measuring a finger tapping motion and processing a result of the measurement.

BACKGROUND ART

With progress of an aging society, the number of patients with Alzheimer's dementia is increasing year by year, and early detection if possible can delay progress of the disease by medication. Since it is difficult to distinguish between diseases and symptoms associated with aging such as forgetfulness, there may be multiple cases where patients go to a hospital only after the symptoms become severe.

In such a situation, as a screening test for early detection of Alzheimer's dementia, for example, a blood test, an olfactory test, and a test in which a medical interview by a doctor is reproduced on a tablet terminal have been conventionally performed, but there has been a problem such that a subject undergoes a large a burden, such as pain during blood collection and duration of test time. On the other hand, as an examination with a small burden on the subject, a cognitive function evaluation is also performed by button pressing or finger motion measurement of one hand using a tablet terminal, but there is a problem such that sufficient examination accuracy cannot be obtained. If a simple screening test can be performed on a subject with high accuracy with a small burden, it leads to early detection of Alzheimer's dementia, and can also contribute to improvement of the quality of life of patients and reduction in medical cost and care cost.

On the other hand, in recent years, it has been revealed that a motion pattern peculiar to Alzheimer's dementia can be extracted from an opening/closing motion (finger tapping motion) of two fingers by a thumb and an index finger of both hands, and it has been confirmed that there is a high correlation with a dementia test based on motion measurement of the fingers as well as general interview. These are said to be results of capturing a decrease in a rhythm motion function of fingers of both hands which is caused by an atrophy of the brain in Alzheimer's dementia by finger tapping motion measurement. Further, fingers are said to be a second brain, and many regions in a brain are related to functions of fingers, so that movement of fingers is not just related to Alzheimer's dementia, but is also said to be related to dementia such as cerebrovascular disease and Lewy body disease, Parkinson's disease, developmental coordination disorder (such as inability to skip or jump ropes), and the like. In other words, a state of a brain can be known from the tapping motion of fingers. Furthermore, since dexterous motion functions of fingers can be quantified by utilizing the tapping motion of fingers as a "measure" indicating health conditions of the brain, the tapping motion of fingers can be used in various fields such as a healthcare field, a rehabilitation field, and a life support field.

Then, as a method for accurately measuring and evaluating the finger tapping motion, for example, Patent Literature 1 discloses a motion function evaluation system including a motion function measurement apparatus that calculates motion data based on a relative distance between a pair of a transmission coil and a reception coil attached to a movable part of a living body, and an evaluation device that evaluates a motion function of the living body based on motion data received from the motion function measurement apparatus. In other words, Patent Literature 1 discloses that a magnetic sensor attached to a fingertip converts a change in magnetic force fluctuating due to tapping motion of two fingers into an electric signal, and the motion is measured and quantified to capture a feature amount indicating a feature of the motion of fingers to thereby know the state of brain functions.

CITATION LIST

Patent Literature

Patent Literature 1: JP 2016-49123 A

SUMMARY OF INVENTION

Technical Problem

The motion function evaluation system disclosed in Patent Literature 1 can measure and evaluate the finger tapping motion using the magnetic sensor, but it is necessary to measure the finger tapping motion by attaching the magnetic sensor to the fingers, and there is a problem such that it is difficult to measure and evaluate the finger tapping motion at a low cost since an expensive dedicated apparatus for evaluating and analyzing measurement information detected by the magnetic sensor is required.

The present invention has been made in view of the above circumstances, and an object of the present invention is to provide a finger tapping measurement processing terminal, a system, a method, and a computer program capable of measuring and processing the finger tapping motion with good usability at a low cost in a simple form by utilizing a terminal such as a smartphone or a tablet that is widely used without attaching a special dedicated instrument or requiring an expensive dedicated device for evaluating and analyzing the measurement information.

Solution to Problem

In order to solve the problem, the present invention provides a finger tapping measurement processing terminal that measures a finger tapping motion and processes a result of the measurement, the finger tapping measurement processing terminal including:
 a touch panel that is provided on one surface of the terminal, is capable of displaying information related to the finger tapping motion, and is tapped by one of two fingers of a same hand of a user who holds the terminal;
 a finger detector that detects motion of the one finger tapping the touch panel; and
 a processor that performs processing of measuring a two-finger distance during the finger tapping motion between the other of the two fingers holding another surface of the terminal located on an opposite side of the touch panel and the one finger tapping the touch panel based on detection information obtained by the finger detector.

According to the above configuration, due to presence of the finger detector and the processor provided in the terminal with the touch panel, the measurement processing of the finger tapping motion can be performed simply by tapping the touch panel of the terminal with the fingers. Therefore, the measurement processing of the finger tapping motion can be easily performed without attaching a special dedicated instrument and without requiring an expensive dedicated evaluation and analysis apparatus. In particular, if a processor can be achieved by using, for example, a distance measuring sensor or the like already mounted as a permanent component on an existing terminal such as a smartphone or a tablet as a finger detector, and by using an arithmetic circuit of the existing terminal or by newly incorporating the processor into a terminal as, for example, application software, it is also possible to measure and process the finger tapping motion with good usability at a low cost in a simple form by utilizing a terminal such as a smartphone or a tablet that is widely used.

Note that, in the above configuration, the finger detector can detect the motion of fingers using a camera, a distance measuring sensor, or the like. The finger detector may be respectively provided on both sides of the terminal corresponding to respective fingers of both hands of the user who holds both sides of the terminal, or may be provided on one side of the terminal as being common to the respective fingers of both hands of the user. Note that, in a case where a camera is used as the finger detector and positions of the tapping fingers are detected from an image captured by the camera, there is a case where it is difficult to grasp the accurate positions of the fingers due to an imaging angle and an imaging distance. Therefore, it is preferable to acquire in advance, as a reference value, a two-finger target distance serving as a reference of an open position of the finger opening/closing of the finger tapping motion from the image captured by the camera, and calibrate position detection data based on the reference value. In this case, the finger detector may define a reference of the open position of the finger opening/closing of the finger tapping motion using a target length jig having a length corresponding to the two-finger target distance. Further, such a target length jig preferably has transparency that does not hinder detection of the finger detector. Further, when the target length jig is used, in a case where the target length jig is clamped between a surface of the touch panel and the tapping fingers, the fingers can be deformed in a clamped state, and thus it is preferable that a deformation amount is also used for calibration of the position detection data.

Further, in the above configuration, the processor preferably calculates and analyzes the feature amount leading to user's brain function evaluation based on the result of the measurement of the two-finger distance. Furthermore, the processor may evaluate (for example, by a comparison with data of a healthy subject) the user's brain functions and cognitive functions from the calculated feature amount. Such an evaluation is effective as a screening in an early stage for discriminating dementia, and as a matter of course, helps detection of dementia, and can also contribute to determination of judgment in driving a car, for example, and can be applied to a brain training game in a wide range of applications.

Further, in the above configuration, the touch panel is preferably a touch panel display that includes a touch panel for sensing a position of a finger touching a surface of the touch panel and displays information. When such a touch panel display is used, the finger detector can detect the touch of the tapping finger by the touch panel as a closed position of the finger opening/closing of the finger tapping motion.

Further, in the above configuration, it is preferable that the other finger holding the other surface of the terminal is fixed in a state of being in contact with the other surface of the terminal by a fixing part. In this case, the fixing part may be provided on the terminal side, or may be provided as a mounting tool separate from the terminal.

Further, the finger tapping measurement processing terminal having the above configuration may constitute a finger tapping measurement processing system together with a head-mounted information processing apparatus that is mounted on the head of a user who uses the terminal and includes a display unit that displays real space information and virtual space information so as to be visible to the user. In this case, it is preferable that the finger tapping measurement processing terminal and the head-mounted information processing apparatus can communicate with each other via communication means. With the use of the communication means, the head-mounted information processing apparatus can receive information displayed on the display of the finger tapping measurement processing terminal and display the received information on the display unit, for example. Further, in this case as well, it is desirable that the processor of the finger tapping measurement processing terminal can perform processing of calculating and analyzing the feature amount leading to user's brain function evaluation based on the measured two-finger distance. However, it is also possible to cause a remotely provided server apparatus to perform such calculation and analysis. Specifically, for example, such a server apparatus receives the result of the measurement of the two-finger distance from the processor of the finger tapping measurement processing terminal via the communication means, and an arithmetic processor calculates and analyzes the feature amount leading to the user's brain function evaluation based on the received result of the measurement of the two-finger distance. The processing result from the arithmetic processor may be stored in a storage of the server apparatus, and the data stored in the storage may be communicated to the finger tapping measurement processing terminal and the head-mounted information processing apparatus via the communication means.

Further, in addition to the above-described finger tapping measurement processing terminal and the finger tapping measurement processing system, the present invention also provides a method and a computer program for measuring the finger tapping motion and processing the measurement result.

Advantageous Effects of Invention

According to the present invention, due to the presence of the finger detector and the processor provided in the terminal with the touch panel, the finger tapping motion can be measured and processed simply by tapping the touch panel of the terminal with the fingers. Therefore, the finger tapping motion can be easily measured and processed without attaching a special dedicated instrument or requiring an expensive dedicated evaluation and analysis apparatus.

BRIEF DESCRIPTION OF DRAWINGS

FIG. 1 is a perspective view schematically illustrating an appearance of a finger tapping measurement processing terminal according to an embodiment of the present invention having a finger detector on one side.

FIG. 2 is an enlarged cross-sectional view of a part of the finger tapping measurement processing terminal of FIG. 1.

FIG. 3 is a diagram for explaining acquisition of a two-finger target distance in a case where measurement is performed by the finger tapping measurement processing terminal of FIG. 1 using a camera.

FIG. 4 is a diagram for explaining acquisition of the two-finger target distance using a target length jig.

FIG. 5 is a view for explaining acquisition of the two-finger target distance using a target length jig in a capturing manner.

FIG. 6 is a diagram for explaining an operation of acquiring the two-finger target distance using a finger tapping measurement processing terminal including two displays.

FIG. 7 is a diagram illustrating a measurement method in a case where measurement is performed by the finger tapping measurement processing terminal of FIG. 1 using a distance measuring sensor.

FIG. 8 is a perspective view schematically illustrating an appearance of a finger tapping measurement processing terminal including a finger detector on either side.

FIG. 9 is a block diagram illustrating a configuration example of the finger tapping measurement processing terminal illustrated in FIGS. 1 and 8.

FIG. 10 is a flowchart illustrating an example of an operation of the finger tapping measurement processing terminal illustrated in FIGS. 1 and 8.

FIG. 11A is a diagram illustrating an example of measurement data of a finger tapping measurement processing terminal according to an embodiment of the present invention, and FIG. 11B is a diagram illustrating another example of measurement data of the finger tapping measurement processing terminal according to the present embodiment.

FIG. 12 is a perspective view schematically illustrating an appearance of a finger tapping measurement processing system according to an embodiment of the present invention.

FIG. 13 is a block diagram illustrating a configuration example of a head-mounted information processing apparatus constituting the finger tapping measurement processing system in FIG. 12.

DESCRIPTION OF EMBODIMENTS

Hereinafter, an embodiment of the present invention will be described with reference to the drawings.

Note that a finger tapping measurement processing terminal according to an embodiment of the present invention described below is configured as a terminal capable of measuring a finger tapping motion using a touch panel, and while, as illustrated in FIG. 12, a use form (which will be described later) connected to a server 1203 via communication means (network) is conceivable, but any use form may be adopted. Further, the finger tapping measurement processing terminal is configured as a small terminal such as a smartphone in the present embodiment, but may have a form such as a tablet-type thin computer or a personal computer.

Further, in the following embodiments, a finger tapping measurement processing terminal that itself includes a touch panel and can measure and process a finger tapping motion by itself is shown, but the present invention may be embodied as a system or a method that can measure and process a finger tapping motion in cooperation with a separate display, or may be configured as a computer program (for example, a finger tapping motion can be measured using a terminal having a display on one surface, and the measurement result can be displayed on the display) that enables a computer to measure and process such a finger tapping motion or a computer program product storing such a computer program.

A specific embodiment of the present invention is illustrated in FIG. 1, and a finger tapping measurement processing terminal (hereinafter, the terminal may be simply referred to as a terminal) 100 as the illustrated information processing terminal includes a camera 101, a distance measuring sensor 102, and a touch panel 103. The camera 101 and the distance measuring sensor 102 are provided at an edge portion on one side (left side in FIG. 1) of the terminal 100, the camera 101 captures an image of a surrounding object or scene, and the distance measuring sensor 102 is a sensor capable of capturing a shape of an object such as a person or an object as a solid, and can measure a distance and an angle to the object. Further, the touch panel 103 detects a touched position (senses a position of the finger in contact with the surface of the touch panel), and constitutes a touch panel display 103A. Note that the touch panel display 103A is provided on one surface (front surface) of the finger tapping measurement processing terminal 100, and is capable of displaying information related to the finger tapping motion, and as will be described later, the touch panel 103 is tapped by one (the index finger) of two fingers of the same hand of a user who holds the terminal.

In the finger tapping measurement processing terminal 100, one side (one side on the left side in FIG. 1) is held by a left hand 111 of the user, and the other opposing side (one side on the right side in FIG. 1) is held by a right hand 121 of the user. A thumb 112 of the left hand of the user supports a back surface side which is the other surface of the finger tapping measurement processing terminal 100 (surface located on the opposite side of the touch panel 103), and an index finger 113 of the left hand of the user performs an opening/closing motion of opening or closing in a form of contacting the touch panel 103, that is, a tapping motion. Similarly on the other side of the finger tapping measurement processing terminal 100, the thumb 122 of the user's right hand supports the back surface side of the information processing terminal 100, and the index finger 123 of the user's right hand performs an opening/closing motion of opening or closing in contact with the touch panel 103, that is, a tapping motion 124. Note that in FIG. 1, as the left and right index fingers 113 and 123 which perform opening and closing, the index fingers in an opened state are indicated by index fingers 115 and 125, and index fingers in a closed state to be in contact with the touch panel 103 are indicated by index fingers 116 and 126.

In such a state, as finger detector 800 (see FIG. 9) that detects the motion of the index finger 113, 123 tapping the touch panel 103 (the opening/closing motion), specifically, detects motion positions of the index fingers 113 and 123, the camera 101 can capture the positions of the index fingers 113 and 123 from a captured image, and is calibrated based on a predetermined position image (an image in which the index finger is opened at a target distance to be described later) captured in advance, thereby accurately measuring each distance between the index fingers 113 and 123 during the tapping motion and the surface (the surface of the touch panel 103) of the finger tapping measurement processing terminal 100 hanging down over time. Further, the distance measuring sensor 102 can detect each of the distance to the index fingers 113 and 123 and an angle thereof as the finger detector 800, and can measure each distance between the index fingers 113 and 123 performing the tapping motion and the surface of the hanging finger tapping measurement processing terminal 100 over time with high accuracy.

Therefore, by taking into account a thickness of the finger tapping measurement processing terminal 100, the distance between the two fingers can be measured between the index finger 113 performing the tapping motion and the left thumb 112 resting on the back surface of the finger tapping measurement processing terminal 100 (holding the back surface). Further, also in a case of the right hand, similarly, in consideration of the thickness of the finger tapping measurement processing terminal 100, it is possible to measure the distance between the index finger 123 during the tapping motion and the thumb 122 of the right hand resting on the back surface of the finger tapping measurement processing terminal 100. As a result, it is possible to measure the tapping motion between the two fingers with good usability in a simple form by using an information processing terminal which is widely spread and inexpensive without wearing a special instrument. Further, based on the measured information, it is possible to analyze and evaluate a feature amount that leads to user's brain function evaluation by an arithmetic function in the finger tapping measurement processing terminal 100, and it is possible to achieve a convenient examination with a small burden on the user for early detection of dementia such as Alzheimer's type, cerebrovascular type, and Lewy body type, Parkinson's disease, developmental coordination disorder (such as an inability to skip or jump ropes), and the like. Furthermore, it is possible to quantify, detect and recognize the dexterous motion functions of the fingers as a "measure" indicating health conditions of the brain based on not only a predictive detection test of dementia or the like but also an analyzed and evaluated feature amount, and thus, it is possible to use it as a training or rehabilitation menu for improving the brain functions. For example, there is a training and rehabilitation menu in which opening and closing of the fingertip is urged according to a sound to evaluate dexterity.

Note that, in the above example, the case where the distance between the index finger and the surface of the finger tapping measurement processing terminal 100 is measured to measure the two-finger tapping motion distance between the index finger and the thumb over time has been described. However, for example, a tapping motion between two other fingers such as a middle finger and the thumb may be performed, and it goes without saying that even if a plurality of fingers is opened and closed, the tapping motion can be measured and similar actions and effects can be obtained. Further, in the following description, a case where the tapping motion is performed with the index finger will be mainly described, but the same applies to cases where a finger other than the index finger is involved.

FIG. 2 illustrates a cross section of a part of the finger tapping measurement processing terminal 100 illustrated in FIG. 1. Note that in FIG. 2, the same components as illustrated in FIG. 1 are denoted by same reference numerals as used in FIG. 1 to omit the description thereof.

FIG. 2 illustrates a cross section of a peripheral portion of the left hand holding the finger tapping measurement processing terminal 100, but the same applies to a cross section of a peripheral portion of the right hand holding the finger tapping measurement processing terminal 100. In FIG. 2, the finger tapping measurement processing terminal 100 includes the touch panel 103, a display unit 201, and a pressure-sensitive sensor 202 on a front surface side forming a display, a pressure-sensitive sensor 203 on a back surface side, and an acceleration sensor 204 and a fixing jig 205 at an edge portion on the same side as the camera 101. The display unit 201 is made of liquid crystal or the like, and displays display contents via the touch panel 103 with high transparency. Further, the pressure-sensitive sensors 202 and 203 sense a contact pressure (a pressing) when the tapping index finger 113 (123) comes into contact with the surface of the touch panel 103, and the acceleration sensor 204 is a sensor that detects acceleration, which is a change in speed per unit time, and can capture motion, vibration, impact, and the like. Further, a sensor that detects not only the acceleration but also a speed and a rotation direction is provided. The fixing jig 205 is a jig that fixes the thumb 112 (142) holding and supporting the finger tapping measurement processing terminal 100, and fixes the thumb 112 (142) in a state of being in contact with the back surface of the terminal 100.

The touch panel 103 can detect a position touched by the index finger 113 (123) and a contact area, and can grasp a positional deviation of the contact. The pressure-sensitive sensor 202 can detect the contact pressure, which is a strength of contact when the index finger 113 (123) touches, and reflect the contact pressure as one of the feature amounts calculated from the finger tapping motion. Further, the pressure-sensitive sensor 203 can detect the contact pressure at which the thumb 112 (142) supporting and holding the finger tapping measurement processing terminal 100 is in contact with the terminal 100, and check whether the thumb 112 (142) is in sufficient contact with the back surface of the terminal 100 and is in a holding state. Further, the fixing jig 205 can firmly support and hold the thumb 112 (142) with respect to the terminal 100 without wobbling at a predetermined position. The acceleration sensor 204 can also measure a force strength when the fingers return by detecting a magnitude and direction of the vibration when the fingers are closed.

Next, a case where the positions of the index fingers 113 and 123 performing the tapping motion is captured by the camera 101 and each distance between the index fingers 113 and 123 and the surface of the hanging finger tapping measurement processing terminal 100 is measured will be described in more detail with reference to FIGS. 3, 4, 5, and 6.

FIG. 3 is a cross-sectional view illustrating a state in which the index fingers 113 and 123 performing the tapping motion is captured by the camera 101. FIG. 4 is a diagram for explaining that the index finger 113 is set in the opened state by the target distance (two-finger target distance) from the surface of the finger tapping measurement processing terminal 100 using a target length jig 401, and the index finger 113 in the opened state by the target distance is captured by the camera 101. FIG. 5 is a view illustrating correction when the finger 113 (115) is dented (deformed) by a contact surface between the target length jig 401 and the index finger 113 (115) generated in the state illustrated in FIG. 4. FIG. 6 is a diagram for explaining that, in a case where the terminal 100 has two screens, the index fingers 113 and 123 is set in the opened state by the target distance from the surface of the finger tapping measurement processing terminal 100 by using the two screens, and the index fingers 113 and 123 in the opened state by the target distance is captured by the camera 101. Note that in FIGS. 3, 4, 5, and 6, the same parts as illustrated in FIGS. 1 and 2 are denoted by same reference numerals as used in FIGS. 1 and 2 to omit the description thereof.

In FIG. 3, the camera 101 disposed on one side (edge portion on the left side in FIG. 3) of the finger tapping measurement processing terminal 100 captures an image of the index finger 113 of the left hand 111 that is near the camera 101 and performs a tapping motion, and a finger tapping motion measurement analysis processor 903 as a processor to be described later in FIG. 9 analyzes and calculates a moving distance (distance from the surface of the terminal 100 . . . thus, the two-finger distance) 311 of the index finger 113 by the opening and closing from the captured image of the index finger 113 (that is, the detection information or the position detection data obtained by the finger detector 800). Further, the camera 101 captures an image of the index finger 123 of the right hand 121 that is far from the camera 101 and performs the tapping motion, and the finger tapping motion measurement analysis processor 903 analyzes and calculates a moving distance 321 by the opening and closing of the index finger 123 from the captured image of the index finger 123. Here, since the camera 101 and the distance measuring sensor 102 need to measure up to the surface of the display in order to detect the contact of the fingers, an angle of view of the camera 101 and the distance measuring sensor 102 may be changed so as to be reflected up to near the surface by changing a lens position or the like.

Incidentally, it is difficult to grasp the distances 311 and 321 of the index fingers 113 and 123 moving by the tapping motion accurately only by the positions and sizes of the index fingers 113 and 123 on the image captured by the camera 101. For example, even if the left and right index fingers 113 and 123 perform the opening/closing motion at the same distance, the index finger 113 of the left hand 111 close to the camera 101 appears larger than the index finger 123 far from the camera 101 on the image captured by the camera 101, and the distance of the opening/closing motion is also seen longer. Therefore, it is difficult to accurately measure the distance of the opening/closing motion performed by the left and right index fingers 113 and 123 as it is. Therefore, in the present embodiment, before photographing the index fingers 113 and 123 to measure the distance between the index fingers 113 and 123 and the surface of the finger tapping measurement processing terminal 100, the index fingers 113 and 123 are set in advance in a state of opening from the surface of the terminal 100 by a predetermined target distance, the index fingers 113 and 123 in the set state are captured by the camera 101, the finger detector 800 including the camera 101 identify and recognize the target distance between the index fingers 113 and 123 and the surface of the terminal 100 on the captured image, and the target distance (two-finger target distance) on the image identified and recognized is captured as a length reference (reference value serving as a reference of the open position of the finger opening/closing of the finger tapping motion). Then, when the index fingers 113 and 123 performing the tapping motion are captured and the distance between the index fingers 113 and 123 and the surface of the finger tapping measurement processing terminal 100 is measured, the finger detector 800 calibrate the captured image of the index fingers 113 and 123 based on the previously-fetched length standard, such that the finger tapping motion measurement analysis processor 903 can accurately calculate and measure the distance between the index fingers 113 and 123 and the surface of the terminal 100. Note that there is an optimal distance between two fingers for the evaluation of brain functions by the finger tapping motion, which distance is taken in advance as the predetermined target distance in the present embodiment.

As a specific example of the calibration, as illustrated in FIG. 4, the target length jig 401 having a predetermined target distance between the index finger 113 (115) and the surface of the terminal 100 (having a length corresponding to the two-finger target distance) is clamped between the index finger 115 in the opened state and the surface of the terminal 100, and the index finger 115 in the opened state is captured by the camera 101. Therefore, when the target distance between the index finger 115 and the surface of the terminal 100 is captured as the length reference on the captured image, and the index finger 113 performing the tapping motion is captured, the distance between the captured index finger 113 and the surface of the terminal 100 is calibrated based on the captured length reference, and the distance between the index finger 113 and the surface of the terminal 100 can be measured with high accuracy over time. Then, in consideration of the thickness of the terminal 100 added to the measured distance between the index finger 113 and the surface of the terminal 100, the distance between the two fingers of the index finger 113 and the thumb 112 can be measured over time with high accuracy. Note that referring to FIG. 4, the case of the index finger 115 in the opened state of the left hand 111 has been described, but it goes without saying that the calibration can be similarly performed in the case of the index finger 125 in the opened state of the right hand 121.

In this manner, the finger detector 800 define a reference of the open position of the finger opening/closing of the finger tapping motion using the target length jig 401, but the target length jig 401 is formed of a material having transparency at a level that does not block the capturing operation of the camera (that does not block the detection of the finger detector 800). As a result, even if there is the target length jig 401, the camera 101 can capture the motion of the index finger through the target length jig 401, and in particular, it is possible to avoid that the target length jig 401 set for the left hand obstructs the motion capturing of the index finger 123 of the right hand far from the camera 101.

Further, when the target distance between the index finger 113 and the surface of the terminal 100 is measured using the target length jig 401, the index finger 115 pressing the target length jig 401 in the opened state is in a flat state (deformed state) in which an original bulge of a contact surface 501 with the target length jig 401 is recessed by a pressing force as illustrated in FIG. 5, and an error occurs in the distance between the index finger 115 and the surface of the terminal 100 by a recess (deformation amount) 502. Therefore, in the present embodiment, in order to achieve a predetermined target distance 503 when the index finger 113 is in the opened state, a length of the target length jig 401 is set to a length increased by the recess 502. As a result, the length reference for calibration can be accurately taken, and thus, the distance between the index finger and a terminal surface can be measured over time with higher accuracy. In other words, in the present embodiment, the finger detector 800 detect the deformation amount of the finger that deforms in a state where the target length jig 401 is clamped between the surface of the display and the tapping finger, and calibrate the position detection data based on a deformation amount detection value.

As still another specific example of the calibration, as illustrated in FIG. 6, in a case where the terminal 100 has two screens of a fixed display screen 601 and a display screen 602 to be opened and closed, the index finger 113 of the left hand 111 is opened on the fixed display screen 602 to be like the index finger 115 in the opened state while the display screen 601 to be opened and closed is in the opened state. Then, the index finger 115 is brought to a position with a target height so as to be aligned while viewing a standard of "the position of the target height when the index finger is opened" indicated by display contents 603 on the display screen 602 to be opened and closed. Therefore, the index finger 115 can be set in accordance with the position of the distance 604 of the target height from the surface of the terminal 100. When the index finger 115 is captured by the camera 101 in this state, the target distance between the index finger 115 and the surface of the terminal 100 on the captured image can be taken as the length reference. Further, similarly in the case of the index finger 123 of the right hand 121, the index finger 125 is brought to the position of the target height while viewing the standard of "the position of the target height when the index finger is opened" indicated by display contents 605 on the display screen 602 to be opened and closed, and the index finger 125 can be set according to the position of a distance 606 of the target height from the surface of the terminal 100. When the index finger 125 is captured by the camera 101 in this state, the target distance between the index finger 125 and the surface of the terminal 100 on the captured image can be taken as the length reference. Therefore, when the index finger performing the tapping motion is captured, the distance between the captured index finger and the surface of the terminal 100 can be calibrated based on the length reference taken in advance, and as a result, the distance between the index finger and the surface of the terminal 100 can be measured with high accuracy over time. Furthermore, the distance between the two fingers of the index finger and the thumb can be measured with high accuracy over time by taking into consideration of the thickness of the terminal 100 to the measured distance between the index finger and the surface of the terminal 100.

Next, a case where the position of the index fingers 113 and 123 performing the tapping motion is captured by the distance measuring sensor 102 and each distance between the index fingers 113 and 123 and the surface of the hanging finger tapping measurement processing terminal 100 is measured will be described in more detail with reference to FIG. 7. FIG. 7 is a cross-sectional view illustrating a state in which the distance and the angle between the index fingers 113 and 123 performing the tapping motion are detected by the distance measuring sensor 102. Note that in FIG. 7, the same parts as illustrated in FIGS. 1, 2, 3, 4, 5, and 6 are denoted by same reference numerals as used in FIGS. 1, 2, 3, 4, 5, and 6 to omit the description thereof.

In FIG. 7, the distance measuring sensor 102 arranged on one side (the edge portion on the right side) of the terminal 100 detects a distance Llc to the index finger 113 of the left hand 111 performing the tapping motion near the distance measuring sensor 102 and an angle θ1 thereof. A distance Lla between the index finger 113 and the surface of the terminal 100 can be calculated by Llc×sin θ1 from the detected distance Llc and angle θ1, such that the distance Lla between the index finger 113 performing the tapping motion and the surface of the terminal 100 can be measured over time. Further, similarly for the index finger 123 of the right hand 121, the distance measuring sensor 102 detects the distance Lrc to the index finger 123 of the right hand 121 that is at a position away from the distance measuring sensor 102 and performs the tapping motion and an angle θr thereof. A distance Lra between the index finger 123 and the surface of the terminal 100 can be calculated by Lrc×sin θr from the detected distance Lrc and angle θr, such that the distance Lra between the index finger 123 performing the tapping motion and the surface of the terminal 100 can be measured over time. Furthermore, the distance between the index finger and the thumb can be measured with high accuracy over time by taking into consideration of the thickness of the terminal 100 to the measured distance between the index finger and the surface of the terminal 100. Further, by detecting the position where the index fingers 113 and 123 come into contact with the touch panel 103 and combining the detection with the detection of the distance to the finger by the distance measuring sensor 102, it is possible to measure a passage of time from separation from the touch panel 103 to a return and contact again as well as a trajectory of the motion of the index fingers 113 and 123 during that time with high accuracy. As described above, in the present embodiment, the finger detector 800 can detect the position of the tapping finger based on the distance and the angle detected by distance measuring sensor 102, and the finger tapping motion measurement analysis processor 903 can measure the two-finger distance based on position detection information.

Next, a case where one camera 101 and one distance measuring sensor 102 are provided on each of the opposite sides of the terminal 100 (the finger detector is provided on either side of the terminal 100) will be described with reference to FIG. 8.

FIG. 8 illustrates the finger tapping measurement processing terminal 100 in which the camera 101 and the distance measuring sensor 102 are provided on one side of the terminal 100, and the camera 801 and the distance measuring sensor 802 are also provided on the other side facing the terminal. Note that in FIG. 8, the same parts as illustrated in FIGS. 1, 2, 3, 4, 5, 6, and 7 are denoted by same reference numerals as used in FIGS. 1, 2, 3, 4, 5, 6, and 7 to omit the description thereof.

In a case where the camera 101 and the distance measuring sensor 102 are provided only on one side of the terminal 100 as illustrated in FIG. 1 described above, since the left hand 111 is located near the camera 101 and the distance measuring sensor 102, the distance between the index finger 113 of the left hand 111 and the surface of the terminal 100 is relatively easily and accurately measured. However, since the right hand 121 is located far from the camera 101 and the distance measuring sensor 102, it may be difficult to relatively easily and accurately measure the distance between the index finger 123 of the right hand 121 and the surface of the terminal 100. On the other hand, as illustrated in FIG. 8, newly adding the camera 801 and the distance measuring sensor 802 to the other side near the right hand 121 allows the distance between the index finger 123 of the right hand 121 and the surface of the terminal 100 to be measured relatively easily and accurately by the camera 801 and the distance measuring sensor 802 near the right hand 121. In other words, with respect to both the left hand and the right hand, it is possible to accurately measure the distance between the index finger and the terminal surface by a nearby camera and a distance measuring sensor, so that the distance between the index finger and the terminal surface can be measured more accurately without being disturbed by the index finger of the other hand. In other words, according to FIG. 8, the finger detector 800 can detect the motion of the tapping finger of each of both hands of the user who holds the terminal 100 on both sides thereof, and the finger tapping motion measurement analysis processor 903 can perform processing of measuring the two-finger distance for each of both hands of the user.

Further, in FIGS. 1 and 8, the operations of each of the camera 101 and the distance measuring sensor 102 in a case where the camera 101 and the distance measuring sensor 102 are provided on one side or two sides above and below (or right and left) the terminal 100 have been described.

However, the finger motion during the tapping motion may be simultaneously captured and detected by the camera 101 and the distance measuring sensor 102. As a result, for example, in a situation where two fingers overlap or one of the fingers cannot be seen as viewed from the camera 101 or the distance measuring sensor 102, the camera 101 and the distance measuring sensor 102 positioned to be shifted can measure the finger motion while complementing each other, and an effect that the motion positions of the left and right fingers can be accurately measured without leaking can be obtained. Naturally, it goes without saying that the accuracy is enhanced by using the camera 101 and the distance measuring sensor 102 together even during normal measurement.

FIG. 9 illustrates a block diagram of a configuration of the finger tapping measurement processing terminal 100 according to the present embodiment. In FIG. 9, the terminal 100 includes first and second cameras 101, 801, first and second distance measuring sensors 102, 802, first and second pressure-sensitive sensors 202 and 203, the acceleration sensor 204, a gyro sensor 901, a geomagnetic sensor 902, a finger tapping motion measurement analysis processor 903, a controller 904, a memory 910 including a program 911 and information data 916, the touch panel 103, the display unit 201, a microphone 931, a speaker 932, a vibration generator 933, a transceiver 934, and a transmission/reception antenna 935, and these components are connected to one another via a bus 950 except for the transmission/reception antenna 935. In this case, the first and second cameras 101, 801, the first and second distance measuring sensors 102, 802, the first and second pressure-sensitive sensors 202, 203, and the touch panel 103 constitute the finger detector 800 that detects finger motion that taps the display.

The first camera 101 is installed on one side along an up-down direction (or left-right direction) of the terminal 100, and the second camera 801 is installed on the other side along the up-down direction (or left-right direction) of the terminal 100, and they capture a field of view state in front mainly of the user's fingers. In the case of FIGS. 1 and 3, the index fingers 113, 123 of the left hand and the right hand performing the tapping motion are captured by the first camera 101. In the case of FIG. 8, the index finger 113 of the left hand performing the tapping motion is captured by the first camera 101, the index finger 123 of the left hand performing the tapping motion is captured by the second camera 801, and the captured images are taken in the terminal 100.

The first and second distance measuring sensors 102 and 802 are sensors capable of capturing a shape of an object such as a person or a solid. Examples of such sensor include a light detection and ranging (LiDAR) sensor that irradiates an object with laser light such as infrared light, measures reflected scattered light, and analyzes and detects a distance to the object at a long distance and a state of the object; a time of flight (TOF) sensor that measures reflection time of pulsed light applied to the object for each pixel and measures a distance; and a millimeter wave radar that emits a millimeter wave, captures the reflected wave, and detects a distance to the reflected object and a state of the object. In the case of FIGS. 1 and 7, the index fingers 113, 123 of the left hand and the right hand performing the tapping motion is captured by the first distance measuring sensor 102, and the distance to each of the index fingers 113 and 123 and the angle thereof are detected. In the case of FIG. 8, the distance and angle of the index finger 113 of the left hand performing the tapping motion can be detected by the first distance measuring sensor 102, and the distance and angle of the index finger 123 of the right hand performing the tapping motion can be detected and taken into the terminal 100 by the second distance measuring sensor 802.

The first and second pressure-sensitive sensors 202 and 203 are sensors that detect the pressure (the contact pressure) generated by contact. The first pressure-sensitive sensor 202 is provided below the touch panel 103 and the display unit 201 on the surface side of the terminal 100, and can detect a contact pressure when an opening/closing finger contacts the surface of the terminal 100, determine that the opening/closing finger has closed to the terminal surface, and measure a strength of contact when the opening/closing finger closes and abuts on the terminal surface. On the other hand, the second pressure-sensitive sensor 202 is provided on the back surface of the terminal 100, detects the contact pressure from the thumb abutting on the back surface of the terminal, can determine whether the thumb firmly holds the terminal 100, and can measure the strength of holding by the thumb. Further, pressures of the first pressure-sensitive sensor 202 and the second pressure-sensitive sensor 203 can be combined to obtain a pressure strength when the finger is closed.

The acceleration sensor 204 is a sensor that detects acceleration, which is a change in speed per unit time, and can capture, for example, motion, vibration, and impact. By detecting the magnitude and direction of the vibration when the finger is closed using the acceleration sensor 204 provided in the terminal 100, the strength of the force when the finger returns and the force strength when the finger touches can also be measured. Further, the gyro sensor 901 is a sensor that detects an angular velocity in a rotation direction, and can capture states of vertical, horizontal, and oblique postures. Therefore, the motion of the terminal 100 can be detected using the acceleration sensor 204 and the gyro sensor 901 mounted on the terminal 100. The geomagnetic sensor 902 is a sensor that detects the magnetic force of the Earth, and detects the direction in which the terminal 100 is facing. It is also possible to detect the motion of the terminal 100 by capturing a geomagnetic change with respect to the motion of the terminal 100 using a three-axis type that detects geomagnetism in a vertical direction in addition to a front-rear direction and the left-right direction as a geomagnetism sensor. As a result, it may be detected and determined whether an arrangement state is such that the display screen of the terminal 100 is visible.

The finger tapping motion measurement analysis processor 903 analyzes the position of the finger performing the tapping motion from the motion information of the finger captured by the first and second cameras 101 and 801 and the motion information of the finger detected by the first and second distance measuring sensors 102 and 802, and measures the two-finger distance of the finger (for example, the index finger) performing the tapping motion and the finger that keeps still (for example, the thumb). Further, the finger tapping motion measurement analysis processor 903 also performs processing of calculating and analyzing the feature amount indicating the feature of the finger motion in each item of the distance, the speed, the acceleration, the jerk, a tap interval, and a phase difference based on the information on measured two-finger distance which is temporally displaced by the tapping motion. The calculated and analyzed feature amount leads to the evaluation of the user's brain functions, so that the state of the brain can be known, and it is possible to perform an examination for early detection of dementia such as Alzheimer's type, cerebrovascular type, and Lewy body type, Parkinson's disease, developmental coordination disorder (such as inability to skip or jump ropes), and the like. Further, the calculated and analyzed feature amount makes it possible to quantify, detect and recognize the dexterous motion functions of the fingers as a "measure" indicating the health conditions of the brain. In the item of the distance of feature amount, a maximum shake width of the finger, a total moving distance, and the like are calculated, and how the magnitude of the finger motion has changed is evaluated. In the item of the speed of feature amount, the maximum speed, an opening speed, a closing speed, and the like are calculated, and how fast the finger moves is evaluated. In the item of the acceleration of feature amount, a maximum amplitude of the acceleration, a momentum to start opening, a momentum to finish opening, a momentum to finish closing, a momentum to start closing, finger contact time, and the like are calculated, and a momentum of the finger motion is evaluated. In the item of the tap interval of feature amount, number of taps, a tap cycle, and the like are calculated, and a tapping timing and its variation are evaluated. In the item of the phase difference of feature amount, shifting of both hands, similarity of both hands, and the like are calculated, and cooperation between both hands is evaluated.

The controller 904 is constituted by, for example, a CPU, and executes the program 911 such as an operating system (OS) 912 and various operation control applications 913 and 914 stored in the memory 910, thereby performing operation control processing of the entire terminal 100 and controlling an activating operation of various applications.

The memory 910 includes, for example, a flash memory, and stores the program 911 such as the operating system 912 and the operation control applications 913, 914 for various processes of, for example, image, audio, document, display, and measurement. The memory 910 also stores the information data 916 such as base data 917 necessary for basic operations by, for example, the operating system 912, and file data 918 and 919 used by, for example, the various applications 913, 914. For example, the image processing application is activated, an image is captured by the camera, and captured file data is stored. Note that the processing in the finger tapping motion measurement analysis processor 903 may be stored as one application A, and the measurement of the two-finger distance accompanying the finger tapping motion and a calculation analysis of the feature amount may be processed by an activating of the application A. Further, the two-finger distance measured from the information processing terminal may be received by an external server apparatus having high calculation performance and a large capacity, and the feature amount may be calculated and analyzed.

The display unit 201 includes, for example, a liquid crystal panel, and displays an image and a video as well as notification information to the user such as a remaining amount of battery capacity, various alarms, and time, as well as an icon of an application to be activated on the display screen. In particular, in the present embodiment, the processing result processed by the finger tapping motion measurement analysis processor 903 can be displayed.

The touch panel 103 is made of a highly transparent material, and detects a position and an area on a screen touched by the finger. The touch panel is provided on the surface of the information processing terminal 100, and can determine that an opened or closed index finger is closed and touches the surface of the terminal 100. Further, an input operation can be performed by touching the touch panel 103 while viewing an icon or the like displayed on the display unit 201. For example, the touch panel 103 is a touch pad type input means such as a capacitance type input means, and can detect an approach or a touch operation by a finger, a touch pen, or the like as an operation input, and can set and input information desired to be input by the user, and can easily select and designate an icon of an application or a file on a display screen by the touch operation. Then, in the present embodiment, the finger detector 800 can detect the contact of the tapping finger by the touch panel 103 as the closed position of the finger opening/closing of the finger tapping motion.

A microphone 931 collects a voice from outside or from the user's own vocalization, and a speaker 932 outputs a voice to the outside to inform the user of a voice such as the notification information or music. Further, an instruction related to finger tapping measurement may be transmitted to the user by voice using the speaker.

A vibration generator 933 generates vibration under the control of the controller 904, and converts the notification information to the user transmitted by the information processing terminal 100 into vibration. The vibration generator 933 applies the vibration generated to the finger or the like holding the information processing terminal 100, and can reliably transmit the notification to the user.

The transceiver 934 is a communication interface that performs wireless communication with, for example, the server apparatus in another place by short-distance wireless communication, wireless LAN, or base station communication, and transmits and receives, for example, measurement data, and analyzed and calculated feature amounts to and from, for example, the server apparatus via the transmission/reception antenna 935 during wireless communication. Note that, the short-range wireless communication is performed using, for example, an electronic tag, but is not limited thereto, and may be performed using a wireless LAN such as Bluetooth (a registered trademark), IrDA (Infrared Data Association, a registered trademark), Zigbee (registered trademark), HomeRF (Home Radio Frequency, registered trademark), or Wi-Fi (registered trademark) as long as the wireless LAN can perform at least wireless communication when the wireless LAN is near another information terminal. Further, as the base station communication, wireless communication over a long distance such as Wideband Code Division Multiple Access (W-CDMA) or Global System for Mobile communications (GSM) (registered trademark) may be used. Note that it is also possible to detect a positional relationship and an orientation between the terminals by using an ultra wide band (UWB). Although not illustrated, the transceiver 934 may use another method such as communication using an optical communication sound wave as wireless communication means. In this case, instead of the transmission/reception antenna 935, a light emitter/receiver and a sound wave output/sound wave receiver are used.

With such components illustrated in FIG. 9, it is possible to measure the distance between two fingers during the tapping motion (for example, the index finger) and the finger (for example, the thumb) on the back surface of the terminal 100, and further, it is possible to calculate and analyze the feature amount representing the feature of finger motion from the information on the measured two-finger distance. Then, the tapping motion between the two fingers can be measured with good usability in a simple form by using an information processing terminal that is widely spread and inexpensive without wearing a special instrument. Further, based on the measured information, it is possible to analyze and evaluate a feature amount that leads to evaluation of the user's brain functions (for example, by the finger tapping motion measurement analysis processor 903 or by an apparatus other than the terminal 100), and to realize a convenient examination with a small burden on the user for early detection of dementia such as Alzheimer's type, cerebrovascular type, and Lewy body type, Parkinson's disease, and developmental coordination disorder (such as inability to skip or jump ropes). Furthermore, it is possible to quantify, detect and recognize the dexterous motion functions of the fingers as a "measure" indicating health conditions of the brain based on not only a predictive detection test of dementia or the like but also an analyzed and evaluated feature amount, and thus, it is possible to use it as a training or rehabilitation menu for improving the brain functions.

Next, the operations of the finger tapping measurement processing terminal 100 according to the present embodiment will be further described with reference to FIG. 10.

FIG. 10 is an example of a flowchart for explaining the operations of the finger tapping measurement processing terminal 100 according to the present embodiment. The example is premised on the configuration of FIG. 8, and thus, it is determined whether to measure the two-finger distance by capturing the finger motion performing the tapping motion with the cameras 101, 801 or to measure the two-finger distance by detecting the position of the fingers with the distance measuring sensors 102, 802 (S1001). In a case where the finger motion performing the tapping motion is captured by the cameras 101, 801, before the capturing of the finger performing the tapping motion, a state in which the fingers are opened to the predetermined target distance is set on the terminal 100 (S1002), the fingers are captured by the cameras 101, 108 in this state, and a distance reference of the captured image during the finger tapping motion is acquired from the captured image. Further, the user recognizes a setting state of a finger opened at the predetermined target distance. Therefore, the user can be conscious of opening at the target distance when performing the tapping motion (S1003). After a pre-photographing by the camera, the user enters a tapping exercise for measurement (alternatively, the tapping operation is urged by the computer program) (S1004). On the other hand, in a case where the positions of the fingers are detected by the distance measuring sensors 102, 802, it is not necessary to set the state in which the finger is opened to the predetermined target distance for measuring the two-finger distance in advance before the detection, and the user enters a tapping motion for measurement as it is (S1004). Note that even in the case of detection by the distance measuring sensors 102, 802, by setting the state in which the fingers are opened at the predetermined target distance, it is possible for the user to be aware of opening at the target distance when performing the tapping motion. Needless to say, the calibration may be performed in steps such as S1002 and S1003 even when the distance measuring sensor is used.

As the finger tapping motion, there are a both-hand simultaneous mode in which the finger tapping motion is performed with both hands simultaneously and a both-hand alternating mode in which the finger tapping motion is performed with both hands alternately, and the user executes the finger tapping motion in each mode (tapping step S1005). At this time, the first and second cameras 101, 801 and the first and second distance measuring sensors 102, 802 detect the motion of the tapping finger, and the finger tapping motion measurement analysis processor 903 analyzes the position of the finger performing the tapping motion from the motion information of the finger captured by the first and second cameras 101, 801 and the motion information of the finger detected by the first and second distance measuring sensors 102, 802, and measures the distance between the finger performing the tapping motion and the fixed finger (finger detection step and processing step S1006). In this finger detection step and processing step S1006, the processing in steps S1002 and 1003 described above is reflected, and the operations/processing of the finger detector 800 and the finger tapping motion measurement analysis processor 903 described with reference to FIGS. 1 to 9 are performed. Thereafter, in a case where re-measurement is not necessary (S1007), the finger tapping motion measurement analysis processor 903 calculates and analyzes the feature amount indicating the feature of the finger motion in each item of the distance, the speed, the acceleration, the tap interval, and the phase difference based on the information on measured the two-finger distance temporally displaced by the tapping motion (S1008). Furthermore, the calculated and analyzed feature amounts are displayed on the display unit 201 in a table or a graph for easy understanding, or are uttered by voice from the speaker 932 to notify the user (S1009). In a case where the measurement analysis is not performed again, the process ends (S1010). Note that in a case where re-measurement is necessary, the process returns to step S1004, and in a case where measurement analysis is performed again, the process returns to step S1001. With the above operation, it is possible to accurately measure the two-finger distance during the finger tapping motion and to calculate and analyze the feature amount leading to the user's brain function evaluation based on the measurement result.

FIG. 11A is a diagram illustrating a result measured in the both-hand simultaneous mode in which the finger tapping motion is performed with both hands simultaneously, and FIG. 11B is a diagram illustrating a result measured in the both-hand alternating mode in which the finger tapping motion is performed with both hands alternately. In both figures, a left vertical axis indicates the distance between the finger during the tapping motion (for example, the index finger) and the terminal surface, and a right vertical axis indicates the two-finger distance between the finger during the tapping motion (for example, the index finger) and the finger fixed to the terminal back surface (for example, the thumb), and also indicates the motion of the left hand on an upper side and the index finger of the right hand on a lower side. In the both-hand simultaneous mode, as illustrated in FIG. 11A, the index finger of the left hand and the index finger of the right hand move in the same direction with a lapse of time, but in the both-hand alternating mode, as illustrated in FIG. 11B, it can be seen that the index finger of the left hand and the index finger of the right hand move in opposite directions with the lapse of time, for example, the left index finger is opened and the right index finger is closed when viewed at time 1101. Note that in a case where the motion of the index finger is captured by the camera 101 (801) and the two-finger distance is measured, the measurement is performed in a frame rate unit (60 fps or the like) of the camera 101 (801), and thus a waveform illustrated in FIGS. 11A-11B are a sampling waveform connecting the values of observation points. Here, in a case where the angle of view of the camera is not included up to the surface of the display and the timing of contact with the display cannot be accurately measured, the waveform can be obtained based on the timing of contact with the touch panel.

Next, a finger tapping measurement processing system including the finger tapping measurement processing terminal 100 and a head-mounted information processing apparatus 1201 will be described with reference to FIG. 12.

FIG. 12 illustrates an embodiment of a finger tapping measurement processing system including the finger tapping measurement processing terminal 100, the head-mounted information processing apparatus 1201, and the server apparatus 1203.

In FIG. 12, the head-mounted information processing apparatus 1201 and the finger tapping measurement processing terminal 100, which are mounted on the head of the user who uses the finger tapping measurement processing terminal 100 and include a display processor (display unit) 1235 (see FIG. 13 to be described later) that displays real space information and virtual space information so as to be visible to the user, transmit and receive various types of information via wireless communication or communication means such as an external network. Therefore, the head-mounted information processing apparatus 1201 can receive, from the finger tapping measurement processing terminal 100, information to be displayed on a display screen (display) 1202 of the finger tapping measurement processing terminal 100, finger motion information during tapping motion captured by the camera 101 (801), and the like, as various types of transmission/reception information, and can display, for example, the received information on the display screen 1202, and finger motion information on the display processor 1235 as virtual space information. As a result, during measuring the finger tapping motion, due to a gripping state of the terminal 100 by the thumbs and the index fingers of both hands, as illustrated in FIG. 12, the display screen 1202 of the terminal 100 and the finger performing the tapping motion are blocked by the terminal 100, which is difficult for the user to see but can be clearly viewed by being displayed on the display processor 1235 of the head-mounted information processing apparatus 1201. Further, as transmission and reception of various types of information, an operation explanation related to the finger tapping measurement and instruction information such as start and end of an operation can be transmitted and received between the head-mounted information processing apparatus 1201 to the terminal 100, various instructions can be issued from the head-mounted information processing apparatus 1201 to the terminal 100, and the operation explanation from the terminal 100 can be confirmed by display or voice in the head-mounted information processing apparatus 1201. Note that when the finger tapping measurement processing terminal 100 has display screens on both the front and back surfaces, that is, in a case where there is a display screen also on the back surface, the user can easily view the display screen on the back surface, and an operation guide or the like may be displayed on the display screen on the back surface without using the head-mounted information processing apparatus 1201. Further, in a case where the head-mounted information processing apparatus 1201 is provided with a distance measuring sensor and a camera, and the positions of the left and right index fingers and the thumbs can be detected, the finger tapping motion can be measured only by the head-mounted information processing apparatus 1201.

Further, data may be transmitted and received between the server apparatus 1203 installed outside and the finger tapping measurement processing terminal 100 via wireless communication, and data storage and management may be performed by the large-capacity server apparatus 1203. Further, the two-finger distance, which is measurement data, may be received from the finger tapping measurement processing terminal 100 by the large-capacity server apparatus 1203 having high calculation performance, and the calculation analysis of the feature amount leading to the user's brain function evaluation may be performed. As a result, the calculation analysis of various feature amounts can be performed at a high speed and with high accuracy, and a large amount of feature amount information calculated and analyzed can be stored and managed.

FIG. 13 is a block diagram illustrating a configuration example of the head-mounted information processing apparatus 1201. In FIG. 13, the head-mounted information processing apparatus 1201 includes a camera 1211, a right-eye gaze detector 1212, a left-eye gaze detector 1213, an acceleration sensor 1214, a gyro sensor 1215, a geomagnetic sensor 1216, a distance measuring sensor 1217, a controller 1218, a memory 1220 including a program 1225 and information data 1226, an operation receiver 1234, a display processor 1235, an outer peripheral sound microphone 1236, an utterance sound microphone 1237, a headphone 1238, a vibration generator 1239, a transceiver 1240, and a transmission/reception antenna 1241, and these components are connected to one another via a bus 1250 except for the transmission/reception antenna 1241.

The right-eye gaze detector 1212 and the left-eye gaze detector 1213 detect gazes of the right eye and the left eye, respectively. Note that the processing of detecting a line of sight may use a well-known technique generally used as eye tracking processing. For example, in a method using corneal reflection, there is known a technique of irradiating a face with an infrared light emitting diode (LED) and photographing the face with an infrared camera, and detecting a line of sight based on a position of a pupil with respect to a position of the corneal reflection with a position (corneal reflection) of reflected light generated by irradiation of the infrared LED as a reference point.

The operation receiver 1234 is input means using, for example, a keyboard, a key button, and a touch key, and sets and inputs information desired to be input by the user. The operation receiver 1234 may be provided at a position or in a form in which the user can easily perform an input operation in the head-mounted information processing apparatus 1201, or may be in a form of being separated from a main body of the head-mounted information processing apparatus 1201 and connected in a wired or wireless manner. Further, an input operation screen may be displayed in the display screen of the display processor 1235, and input operation information may be fetched according to the position on the input operation screen to which the line of sight detected by the right-eye gaze detector 1212 and the left-eye gaze detector 1213 is directed, or a pointer may be displayed on the input operation screen and the pointer may be operated by the operation receiver 1234 to fetch the input operation information. Further, the user may utter a voice indicating the input operation, collect the voice with the utterance sound microphone 1237, and capture the input operation information.

In a case of an optically transmissive head-mounted information processing apparatus, the display processor 1235 includes, for example, a projector that projects various types of information such as reproduction information by a start application and the notification information to a user, and a transparent half mirror that forms and displays the projected various types of information in front of the user. Further, in a case of a video transmissive head-mounted information processing apparatus, the head-mounted information processing apparatus includes a display such as a liquid crystal panel that displays a real space object in front of the camera 1211 and various types of information together. As a result, the user visually recognizes and views not only the image in the field of view in front of the user but also image information from the others.

Each of the outer peripheral sound microphone 1236 and the utterance sound microphone 1237 collects a voice from the outside and the user's own utterance. The headphone 1238 is worn on an ear portion of the user to listen to the voice to the user, and can inform the user of the notification information by the voice.

According to the constituent elements in FIG. 13 as described above, by wireless transmission and reception from the finger tapping measurement processing terminal 100 to the head-mounted information processing apparatus 1201, the information on the display screen 1202 of the finger tapping measurement processing terminal 100 can be displayed as the virtual space information by the display processor 1235 in the head-mounted information processing apparatus 1201, and the information such as the operation explanation of the finger tapping measurement can be clearly and visually recognized. Further, the instruction information such as start and end of an operation related to finger tapping measurement can also be transmitted and received between both constituting elements, and various instructions can be issued from the head-mounted information processing apparatus 1201.

Note that the present invention is not limited to the above-described embodiments, and may include various modifications. For example, the above-described embodiments have been explained in detail in order to describe the present invention in an easy-to-understand manner, and are not necessarily limited to those having all the described configurations. Further, the configuration of one embodiment may be partially replaced with the configuration of another embodiment, and the configuration of one embodiment may be additionally equipped with to the configuration of another embodiment. Further, a part of the configuration of each embodiment may be deleted or additionally equipped with or replaced with other configurations.

Further, some or all of the above-described configurations, functions, processors, processing means, and the like may be achieved by hardware, for example, by designing with an integrated circuit. Further, each of the above-described configurations, functions, and the like may be achieved by software through a processor interpreting and executing a program for achieving each function. Information such as a program, a table, and a file for achieving each function may be stored in a recording device such as a memory, a hard disk, and a solid state drive (SSD), or a recording medium such as an IC card, an SD card, and a DVD.

Further, control lines and information lines indicate what is considered to be necessary for the explanation, and do not necessarily indicate all the control lines and the information lines on a product. In practice, it may be considered that almost all the configurations are connected to one another.

Further, in the embodiment described above, a form in which the terminal is held with two fingers of both hands has been described. However, if the terminal is placed on a knee of the user and used, it is possible to easily perform measurement using both hands without holding the terminal with the thumb.

REFERENCE SIGNS LIST

100 Finger tapping measurement processing terminal
101, 801, 1211 Cameras
102, 802, 1217 Distance measuring sensors
103 Touch panel
103A Display
111 Left hand
112, 122 Thumb
113, 123 Index finger
201 Display unit
202, 203 Pressure-sensitive sensor
205 Fixing jig
401 Target length jig
800 Finger detector
903 Finger tapping motion measurement analysis processor (processor)
934, 1240 Transceiver
1201 Head-mounted information processing apparatus
1203 Server apparatus

The invention claimed is:

1. A finger tapping measurement processing terminal that measures a finger tapping motion and processes a result of the measurement, the finger tapping measurement processing terminal comprising:
   a touch panel that is provided on one surface of the terminal, is capable of displaying information related to a finger tapping motion, and is tapped by one of two fingers of a same hand of a user who holds the terminal;
   a finger detector that detects motion of the one finger tapping the touch panel; and
   a processor that performs processing of measuring the two-finger distance during a finger tapping motion between the other of the two fingers holding another surface of the terminal located on an opposite side of the touch panel and the one finger tapping the touch panel based on detection information obtained by the finger detector.

2. The finger tapping measurement processing terminal according to claim 1, wherein the finger detector detects motion of the one finger tapping each of both hands of the user holding the terminal on both sides thereof, and the processor performs processing of measuring the two-finger distance for each of both hands of the user.

3. The finger tapping measurement processing terminal according to claim 2, wherein the finger detector is provided on either side of the terminal.

4. The finger tapping measurement processing terminal according to claim 1, wherein the finger detector includes a camera that captures an image of the one finger to be tapped, the finger detector detects a position of the one finger from the image captured by the camera, and the processor measures the two-finger distance based on position detection data.

5. The finger tapping measurement processing terminal according to claim 4, wherein the finger detector acquires, as a reference value, a two-finger target distance serving as a reference of the open position of finger opening/closing of a finger tapping motion from an image captured by the camera, and calibrate the position detection data based on the reference value.

6. The finger tapping measurement processing terminal according to claim 5, wherein the finger detector defines a reference of the open position of finger opening/closing of a finger tapping motion using a target length jig having a length corresponding to the two-finger target distance.

7. The finger tapping measurement processing terminal according to claim 6, wherein the target length jig has transparency that does not hinder the detection by the finger detector.

8. The finger tapping measurement processing terminal according to claim 6, wherein the finger detector detects a deformation amount of the one finger that deforms while holding the target length jig between the one finger and the surface of the touch panel, and calibrate the position detection data based on a deformation amount detection value.

9. The finger tapping measurement processing terminal according to claim 1, wherein the finger detector includes a distance measuring sensor that detects a distance to the one finger tapping and an angle thereof, detects a position of the one finger based on the distance and the angle detected by the distance measuring sensor, and the processor measures the two-finger distance based on position detection information.

10. The finger tapping measurement processing terminal according to claim 1, wherein
the touch panel is a touch panel display capable of displaying information on a surface of the touch panel, and
the finger detector that detects contact of the one tapping finger as a closed position of finger opening/closing of a finger tapping motion by the touch panel sensing the contact.

11. The finger tapping measurement processing terminal according to claim 1, further comprising a fixing part for fixing the other finger in a state of being in contact with the other surface of the terminal.

12. The finger tapping measurement processing terminal according to claim 1, wherein the touch panel includes a pressure-sensitive sensor that senses a contact pressure when the one tapping finger contacts a surface of the touch panel.

13. The finger tapping measurement processing terminal according to claim 1, wherein the processor performs processing of calculating and analyzing a feature amount that leads to user's brain function evaluation based on the two-finger distance.

14. The finger tapping measurement processing terminal according to claim 1, wherein the touch panel displays a processing result processed by the processor.

15. A finger tapping measurement processing method for measuring a finger tapping motion and processing a result of the measurement, the method finger tapping measurement processing comprising:
a tapping step of tapping a touch panel provided on one surface of a terminal and capable of displaying information related to a finger tapping motion with one of two fingers of a same hand of a user holding the terminal;
a finger detecting step of detecting motion of the one finger tapping the touch panel; and
a processing step of performing a process of measuring a two-finger distance during a finger tapping motion between the other of the two fingers holding another surface of the terminal located on an opposite side of the touch panel and the one finger tapping the touch panel based on detection information obtained in the finger detection step.

16. The finger tapping measurement processing method according to claim 15, wherein the finger detecting step detects a motion of the one finger tapping each of both hands of the user holding the terminal on both sides thereof, and the processing step performs processing of measuring the two-finger distance for each of both hands of the user.

17. The finger tapping measurement processing step according to claim 15, wherein the finger detecting step detects a position of the one finger from an image of a camera that captures the one tapping finger, and the processing step measures the two-finger distance based on position detection data.

18. The finger tapping measurement processing method according to claim 17, wherein in the finger detecting step, the two-finger target distance serving as a reference of the open position of finger opening/closing of a finger tapping motion is acquired as a reference value from an image captured by the camera, and the position detection data is calibrated based on the reference value.

19. The finger tapping measurement processing method according to claim 15, wherein in the finger detecting step, a position of the one finger is detected based on detection data from a distance measuring sensor that detects a distance to the one finger to be tapped and an angle of the distance, and in the processing step, the two-finger distance is measured based on position detection information.

20. The finger tapping measurement processing method according to claim 15, wherein
the touch panel is a touch panel display that displays information on a surface of the touch panel, and
in the finger detecting step, the touch panel detects contact of the one tapping finger as a closed position of finger opening/closing of a finger tapping motion.

21. The finger tapping measurement processing method according to claim 15, wherein in the processing step, processing of calculating and analyzing a feature amount that leads to user's brain function evaluation is performed based on the measured two-finger distance.

22. The finger tapping measurement processing method according to claim 15, wherein the touch panel displays a processing result processed in the processing step.

* * * * *